(12) United States Patent
Cole et al.

(10) Patent No.: US 6,444,195 B1
(45) Date of Patent: Sep. 3, 2002

(54) SUNSCREEN COMPOSITIONS CONTAINING A DIBENZOYLMETHANE DERIVATIVE

(75) Inventors: Curtis Cole, Ringoes; Florence Natter, Hillsborough, both of NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/883,416

(22) Filed: Jun. 18, 2001

(51) Int. Cl.[7] .................... A61K 7/42; A61K 7/44; A61K 7/00
(52) U.S. Cl. .................... 424/60; 424/400; 424/401
(58) Field of Search ................. 424/59, 60, 400, 424/401

(56) References Cited

U.S. PATENT DOCUMENTS

| | | |
|---|---|---|
| 4,668,505 A | 5/1987 | Grollier |
| 4,726,942 A | 2/1988 | Lang et al. |
| 4,925,653 A | 5/1990 | Grollier et al. |
| 5,340,567 A | 8/1994 | Cole et al. |
| 5,346,691 A * | 9/1994 | Ra Spanti et al. ............. 424/59 |
| 5,567,418 A | 10/1996 | Forestier et al. |
| 5,576,354 A * | 11/1996 | De Flandre et al. .......... 424/59 |
| 5,587,150 A | 12/1996 | Deflandre et al. |
| 5,605,680 A | 2/1997 | Deflandre et al. |
| 5,618,520 A | 4/1997 | Hansenne et al. |
| 5,624,663 A | 4/1997 | Deflandre et al. |
| 5,639,446 A | 6/1997 | Raspaunti et al. |
| 5,670,140 A | 9/1997 | Deflandre et al. |
| 5,733,532 A | 3/1998 | Raspanti et al. |
| 5,738,842 A | 4/1998 | Raspanti et al. |
| 5,747,049 A | 5/1998 | Tominaga |
| 5,759,524 A | 6/1998 | Tanner et al. |
| 5,776,439 A * | 7/1998 | Raspanti et al. ............... 424/59 |
| 5,783,173 A | 7/1998 | Bonda et al. |
| 5,783,174 A | 7/1998 | Deckner |
| 5,788,954 A | 8/1998 | Bonda et al. |
| 5,827,508 A | 10/1998 | Tanner et al. |
| 5,849,273 A | 12/1998 | Bonda et al. |
| 5,882,632 A | 3/1999 | Allard et al. |
| 5,882,633 A | 3/1999 | Pisson et al. |
| 5,882,634 A | 3/1999 | Allard et al. |
| 5,928,629 A | 7/1999 | Allard et al. |
| 5,935,556 A | 8/1999 | Tanner et al. |
| 5,951,968 A | 9/1999 | Forestier et al. |
| 5,955,061 A | 9/1999 | Ascione |
| 5,968,485 A | 10/1999 | Robinson |
| 5,972,316 A | 10/1999 | Robinson |
| 5,976,513 A | 11/1999 | Robinson |
| 5,985,250 A | 11/1999 | Hansenne et al. |
| 5,985,925 A | 11/1999 | Josso et al. |
| 5,989,528 A | 11/1999 | Tanner et al. |
| 5,993,788 A | 11/1999 | Hansenne et al. |
| 5,993,789 A * | 11/1999 | Bonda et al. ................. 424/59 |
| 6,033,649 A * | 3/2000 | Gonzenbach et al. ......... 424/59 |
| 6,048,517 A | 4/2000 | Kaplan |
| 6,071,501 A | 6/2000 | Robinson |
| 6,071,502 A | 6/2000 | Forestier et al. |
| 6,077,520 A | 6/2000 | Tuminaga |
| 6,090,369 A | 7/2000 | Stewart |
| 6,129,908 A | 10/2000 | Wunsch et al. |
| 6,126,925 A | 11/2000 | Bonda et al. |

FOREIGN PATENT DOCUMENTS

EP 433086 B2 6/1991

OTHER PUBLICATIONS

Bonda, Craig, et al., "A New Photostabilizer for Full Spectrum Sunscreens", Cosmetics and Toiletries Magazine, vol. 115, No. 6 pp. 37–45 (Jun. 2000).

* cited by examiner

Primary Examiner—Shelley A. Dodson
(74) Attorney, Agent, or Firm—Erin M. Harriman

(57) ABSTRACT

The present invention relates to a method of photostabilizing a composition comprising (a) one or more dibenzoylmethane derivative UV-A absorbing agent(s); (b) one or more benzophenone derivative(s); and (c) a diester or polyester of a naphthalene dicarboxylic acid and a method of protecting mammalian skin or hair from UV radiation comprising topically applying to the skin or hair such a composition.

21 Claims, No Drawings

SUNSCREEN COMPOSITIONS CONTAINING A DIBENZOYLMETHANE DERIVATIVE

FIELD OF THE INVENTION

The present invention relates to sunscreen compositions comprising a dibenzoylmethane derivative, a diester or polyester of a naphthalene dicarboxylic acid and a benzophenone derivative. The sunscreen compositions according to the invention have enhanced photostability.

BACKGROUND OF THE INVENTION

The prolonged exposure to UV radiation, such as from the sun, can lead to the formation of light dermatoses and erythemas, as well as increase the risk of skin cancers, such as melanoma, and accelerate skin aging, such as loss of skin elasticity and wrinkling. Radiation with wavelengths in the UV-A range (from about 320 to 400 nm) and the UV-B range (from about 280 to about 320 nm) can cause such skin damage, and, thus, sunscreen compositions should preferably comprise both UV-A and UV-B absorbers/reflectors (UV sunscreens). Dibenzoylmethane derivatives, the one of the most commonly used UV-A absorbers, however, suffer from photochemical instability, requiring repeated application to the skin to maintain the desired UV-A protection. See, e.g., Kammeyer, et al., Int. J. Cosm. Sci. 9:125–36 (1987).

Others have recognized this stability problem associated with such UV-A absorbers, and have attempted to find means of stabilizing such compounds. See, e.g., U.S. Pat. No. 5,783,173 (using alkylbenzoates), U.S. Pat. No. 5,993,789 (using diester and/or polyesters of naphthalene dicarboxylic acids), U.S. Pat. No. 5,346,691, PCT Application No. WO98/00099, and European Patent No. 845,260 (using trianilino triazine derivatives with or without derivatives of diphenylcyanoacrylic acid), and U.S. Pat. Nos. 5,576,354 and 6,033,649 (using α-cyano-β,β-diphenylacrylate stabilizer), and European Patent Nos. 514,491, 685,222, and 685,225 (using octocrylene, homomenthyl salicylate, octyl salicylate, and 4-methyl benzylidene camphor to stabilize avobenzone).

U.S. Pat. No. 5,776,439 discloses cosmetic compositions useful for the protection of skin and/or hair from ultraviolet radiations containing photostable mixtures of two sunscreen compounds, sunscreen compound (I) and sunscreen compound (II). Sunscreen agents encompassed by compound I include dibenzoylmethane derivatives such as 4-methoxy-4'-tert-butyldibenzoylmethane and 4-isopropyldibenzoylmethane. Sunscreen compound II encompass benzophenone derivatives that were shown to help to stabilize these dibenzoylmethane derivatives. However, there is no teaching or suggestion of the enhanced photostability of the presently claimed compositions as demonstrated by the Examples set forth below.

U.S. Pat. No. 5,993,789 discloses the use of a naphthalene derivative (diethylhexyl 2,6-napthalate "DEHN") in combination with butylmethoxydibenzoylmethane derivatives to photostabilize sunscreen compositions. The patent discusses the use of other commonly utilized sunscreen absorbers in combination with these ingredients (including oxybenzone) to boost the SPF to a level of 20+. This is further disclosed in a publication of Cosmetics and Toiletries (Vol 115: No.6, p. 37–45) with a formulation showing an SPF of 32.8. There is no teaching or suggestion, however, of the enhanced photo-stability of the presently claimed compositions as demonstrated in the Examples set forth below.

SUMMARY OF THE INVENTION

The present invention relates to the discovery that a combination of a benzophenone derivative and a diester or polyester of a naphthalene dicarboxylic acid surprisingly increases the photo-stability of dibenzoylmethane derivatives and thereby provide compositions with increased photostabilization.

Accordingly, in one aspect, the invention features a composition comprising: (a) one or more dibenzoylmethane derivative UV-A absorbing agent(s); (b) a diester or polyester of a naphthalene dicarboxylic acid; and (c) a benzophenone derivative, wherein the diester or polyester of naphthalene dicarboxylic acid and benzophenone derivative are present in an amount sufficient to photo-stabilize the dibenzoylmethane derivative and provide a photo-stable sunscreen composition.

Ideally, the optical absorbance of the sunscreen product would stay high no matter how much it was irradiated with sunlight or any artificial UV source. Sunscreen compositions should maintain protection to the skin upon exposure to both the UVB (290–320 nm) and the UVA (320–400 nm) portions of the UV spectrum. The Sun Protection Factor ("SPF") is a measure of the overall biological protection of the sunscreen product against sunburn reactions. PFA is an analogous measure of protection which evaluates the biological protection in the UVA portion of the spectrum. The PFA of a formulation can be determined from clinical trials (Cole, 1991) or can be estimated with in vitro test models. The retention of the biologically weighted PFA value with increasing exposure to UV light is a measure of the photostability of the UVA filters in the sunscreen composition (of which the dibenzoylmethane derivative sunscreens are particularly unstable.)

Accordingly, what is meant by to photo-stabilize the dibenzoylmethane derivative is that the diester or polyester of naphthalene dicarboxylic acid and benzophenone derivative are present in amounts sufficient for the composition to maintain a proportion of at least 60% of the original PFA value, preferably, with no measurable degradation with high doses ($\geq 50$ Joules/cm$^2$) of sunlight or simulated sunlight exposure.

The present invention also features a method of photostabilizing a sunscreen composition containing dibenzoylmethane derivative UV-A absorbing agent in a composition comprising adding to said composition an effective amount of a diester or polyester of naphthalene dicarboxylic acid and benzophenone derivative.

The present invention also features a method of protecting skin and hair from UV radiation comprising administering the above compositions.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, unless otherwise indicated, all alkyl, alkenyl, and alkoxy groups may be straight or branched chain groups.

The present invention relates to a method of stabilizing a dibenzoylmethane derivative UV-A absorbing agent. What is meant by a dibenzoylmethane UV-A absorbing agent is a compound comprising a dibenzoylmethane group and capable of absorbing radiation in the UV-A range. Examples of dibenzoylmethane derivative UV-A absorbing agent include those of the formula (VII):

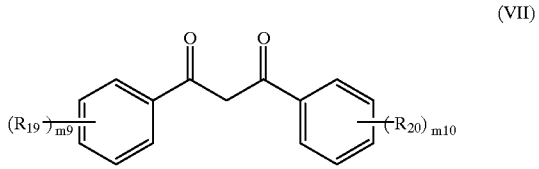

(VII)

wherein $R_{19}$ and $R_{20}$, independently, are $C_1$–$C_8$ alkyl or $C_1$–$C_8$ alkoxy, m9 is 0 to 3, and m10 is 1 to 3. Examples and the synthesis of such compositions are disclosed in U.S. Pat. No. 4,489,057 and include, but are not limited to, 4-(1,1-dimethylethyl)-4'-methoxydibenzoylmethane (avobenzone and sold as PARSOLO® 1789, Roche Vitamins and Fine Chemicals, Nutley, N.J., USA), 2-2'-methyldibenzoylmethane, 4-methyl-dibenzoylmethane, 4-isopropyldibenzoylmethane, 4-tert-butyldibenzoylmethane,4-tert-butyl-4'-methoxydibenzoylmethane, 2,4-dimethylbenzoylmethane, 2,5-dimethylbenzoylmethane, 4,4'-diisopropylbenzoylmethane, 2-methyl-5-isopropyl-4'-methoxy-dibenzoylmethane,2-methyl-5-tert-butyl-4'methoxydibenzoyl-methane, 2,4-dimethyl-4'-methoxydibenzoylmethane, and 2,6-dimethyl-4-tert-butyl-4'-methoxydibenzoylmethane. Generally, the dibenzoylmethane derivative UV-A absorbing agent is present in an amount from about 0.1% to about 20%, preferably from about 0.1 to about 10%, more preferably, from about 1 to about 3% by weight, of the composition.

Examples of diesters and polyesters of a naphthalene dicarboxylic acid are compounds of formulae (X) or (XI):

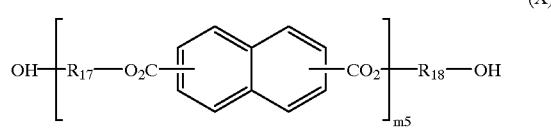

(X)

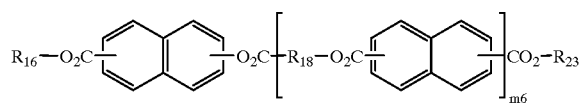

(XI)

wherein $R_{16}$ and $R_{23}$, independently, are selected from the group consisting of a $C_1$–$C_{22}$ alkyl, a diol having the structure HO—$R_{18}$—OH, and a polyglycol having the structure HO—$R_{17}$—(—O—$R_{18}$—)$_{m5}$—OH; $R_{17}$ and $R_{18}$, independently, are $C_1$–$C_6$ alkenyl; and m5 and m6, independently, are each in the range of 1 to about 100. Examples, including the synthesis, of such diesters or polyesters of naphthalene dicarboxylic acid are described in U.S. Pat. No. 5,993,789, and include, but not limited to, diethylhexyl naphthalate (HallBrite® TQ, C.P. Hall Company, Bedford Park, Ill., USA). See Bonda, et al., Allured's Cosmetic & Toiletries Magazine, 115(6):37–45 (2000) disclosing the uses of such compounds in sunscreen compositions. The diester or polyester of naphthalene dicarboxylic acid is generally present in an amount from about 0.1% to about 20%, by weight, of said composition (e.g., about 0.5% to about 10%, by weight, of the composition).

Examples of benzophenone derivatives include those known in the art to provide protection of the skin from UV radiation, for example,such as taught by U.S. Pat. No. 5,776,439. Preferred compounds include 2-hydroxy-4-methoxybenzophenone ("oxybenzone") and 2-hydroxy-4-methoxybenzophenone-5-sulfonic acid ("sulisobenzone") and 2-2'dihyroxy-4-methoxybenzophenone ("dioxybenzone").

The benzophenone derivative is present in an amount from about 0.5% to about 6%, by weight, of said composition preferably from about 3 to about 6% by weight of the composition.

As discussed above, the compositions according to the invention comprise a dibenzoylmethane derivative, a diester or polyester of naphthalene dicarboxylic acid and a benzophenone derivative wherein the diester or polyester of naphthalene dicarboxylic acid and the benzophenone derivative are present in amounts sufficient for the composition to maintain a proportion of at least 60% of the original PFA value, preferably, with no measurable degradation with high doses ($\geq 50$ Joules/cm$^2$ of sunlight or simulated sunlight exposure. In a particularly preferred embodiment, at least 65%, more preferably, at least 70%, more preferably, at least 75%, more preferably at least 80%, and most preferably, at least 85% of the original PFA value is maintained.

In another embodiment, the composition further comprises one or more additional UV-A and/or UV-B absorbing/reflecting agent(s) that are known in the art provided that the composition is capable of providing the photostability described above, i.e., a PFA value after exposure to at least 50 Joules/cm$^2$ of simulated sunlight that is minimally 60% of the original PFA value before exposure. Suitable additional agents are taught for example by U.S. application Ser. Nos. 09/688,651, 09/688,652, and 09/688,653, each filed Oct. 16, 2001.

Examples of such absorbing/reflecting agents include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzophenone derivatives such as dioxybenzophenone and sulisobenzophenone; benzoic acid derivatives such as aminobenzoic acid and octyldimethyl para-amino benzoic acid; octocrylene; dioctyl butamido triazone, titanium dioxide; zinc oxide; iron oxides; octyl triazone; butyl methoxydibenzoyl methane; drometrizole trisiloxane; and menthyl anthranilate. Other UV absorbers/reflectors useful herein can be found in Sagarin, Cosmetics Science and Technology, Chapter VIII, pages 189 et seq. and the ICI Handbook page 1672. A list of such compounds is also disclosed in U.S. Pat. No. 4,919,934. The individual UV absorbing/reflecting agent concentration can range from about 0.1% to about 30%, by weight, of the composition. The total concentration of all such agents should be based on the desired sunscreen protection factor ("SPF") level (e.g., an SPF level of from about 10 to about 60). An additional benefit of the photostabilization of the sunscreen actives is that lower amounts of the sunscreen absorbers are needed to achieve the same protection levels (both SPF and PFA) and the potential for skin irritation is therefore reduced.

In one embodiment, the compositions of the present invention further comprise one or more other cosmetically active agent(s). What is meant by a "cosmetically active agent" is a compound that has a cosmetic or therapeutic effect on the skin, e.g., agents to treat wrinkles, acne, or to lighten the skin. In one embodiment, the agent is selected from, but not limited to, the group consisting of: alkanolamines, hydroxy acids; benzoyl peroxide; sulfur resorcinol; D-panthenol; hydroquinone; anti-inflammatory agents; skin lightening agents; antimicrobial and antifungal agents such a miconazole, ketoconazole, and elubiol; vitamins such as ascorbic acid; tocopherols and tocotrienols such as tocopheryl acetate; retinoids such retinol, retinal, retinyl palmitate, retinyl acetate, and retinoic acid; hormones such as estrogens and dihydroxyandrostene dione; 2-dimethylaminoethanol; lipoic acid; amino acids such a proline and tyrosine; lactobionic acid; self-tanning agents such as dihydroxy acetone; dimethyl aminoethanol; acetyl-coenzyme A; niacin; riboflavin; thiamin; ribose; electron transporters such as NADH and FADH2; botanical extracts such as ginkgo biloba, aloe vera, and soy; and derivatives thereof. The cosmetically active agent will typically be present in the composition of the invention in an amount of from about 0.001% to about 20% by weight of the composition, e.g., about 0.01% to about 10% such as about 0.1% to about 5% by weight of the composition.

Examples of hydroxy acids include, but are not limited, to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The compositions of the present invention may also comprise one or more of the following: antioxidants (e.g., ascorbic acid, tocopherols, polyphenols, tocotrienols, BHA, and BHT), chelating agents (e.g., EDTA), and preservatives (e.g., parabens). Examples of suitable antioxidants, preservatives, and chelating agents are listed in pp. 1612–13, 1626, and 1654–55 of the ICI Handbook. In addition, the topical compositions useful herein can contain conventional cosmetic adjuvants, such as dyes, opacifiers (e.g., titanium dioxide), pigments, and fragrances.

The compositions of the present invention can be used by topically administering it to a mammal, e.g., by the direct laying on or spreading of the composition on the skin or hair of a human. The cosmetic compositions useful in the subject invention, thus, involve formulations suitable for topical application to mammalian skin or hair, the formulation comprising (i) dibenzoylmethane derivative(s), (ii) a diester or polyester of a naphthalene dicarboxylic acid, (iii) a benzophenone derivative; and (iv) optionally, other compounds/agents such as the other UV-A or UV-B absorbers/reflectors listed herein, and/or other cosmetically active agents and (v) a cosmetically-acceptable topical carrier. The term "cosmetically-acceptable topical carrier" refers to a carrier for topical use that is capable of having the dibenzoylmethane, the diester or polyester of a naphthalene dicarboxylic acid, the benzophenone derivative and any other agents dispersed or dissolved therein, and possessing acceptable safety properties.

The topical compositions useful in the present invention may be used for a variety of cosmetic uses, including, but not limited to, protection the skin or hair from UV radiation. The compositions, thus, may be made into a wide variety of product types. These include, but are not limited to lotions, creams, gels, sticks, sprays, ointments, mousses, and cosmetics/make-up. These products may comprise several types of carrier systems including, but not limited to single phase solutions (e.g., oil based solutions), emulsions, and gels. In another embodiment, the compositions according to the invention can be impregnated onto a dry or wet wipe by means known in the art. The compositions of the present invention may be prepared using methodology that is well known by an artisan of ordinary skill. The following is a description of the manufacturing of cosmetic compositions of the present invention. Other compositions of the invention can be prepared in an analogous manner by a person of ordinary skill in the art.

EXAMPLE 1

Testing of Formulations Containing Dibenzoylmethane Derivatives

The sunscreen containing composition base of Table I was used in the following experiments to test the photostability of the formulations containing a dibenzoylmethane derivative UV-A absorber.

TABLE I

| INGREDIENT | % (W/W) |
|---|---|
| WATER | q.s. 100 |
| ACRYLATES C10–30 ALKYL ACRYLATE COPOLYMER | 0.2 |
| TRIETHANOLAMINE | 0.65 |
| DISODIUM EDTA | 0.1 |
| HOMOSALATE | 12 |
| BUTYL METHOXYDIBENZOYLMETHANE | 3.0 |
| OCTYL SALICYLATE | 5 |
| CETYL PHOSPHATE | 0.5 |
| SORBITAN ISOSTEARATE | 1.5 |
| CETYL ALCOHOL | 1.5 |
| STEARIC ACID | 1.5 |
| ISOSTEARIC ACID | 1.5 |
| PRESERVATIVE MIXTURE | 1.5 |

The acrylates C10–30 alkyl acrylate coplymer was first dispersed in the water in a first container and then neutralized with triethanolamine. The dispersion was then heated to 80–85° C. during which time the disodium EDTA was added. The homosalate, octyl salicylate, and avobenzone were added to and mixed in a second container, and slowly heated. Once the solution was clear, the remaining ingredients were added to and mixed with the clear solution. The preservative mixture was obtained from Collaborative Group (East Setauket, N.Y., USA) under the trade name Germazide® MPV. Once both phases reached 85° C., the ingredients in the second container were added to the first container and mixed for ten minutes. The resulting emulsion was then cooled to 45° C., and mixed in a homomixer for one minute.

To this formulation base, the following additional ingredients, in the amounts indicated in Table II, were added initially to the second container: oxybenzone (benzophenone-3); diethylhexyl naphthalate ("TQ") (HallBrite TQ®, C.P. Hall Co.):

TABLE II

| FORMULATION NO. | ADDED INGREDIENT(S) (% W/W) |
|---|---|
| 1 (9576-015) | NONE |
| 2 (9567-065) | Benzophenone-3 (3%) |
| 3 (9567-066) | Benzophenone-3 (6%) |
| 4 (9576-028) | TQ (5%) |

TABLE II-continued

| FORMULATION NO. | ADDED INGREDIENT(S) (% W/W) |
|---|---|
| 5 (9576-047) | TQ (5%) + benzophenone-3 (1%) |
| 6 (9576-046) | TQ (5%) + benzophenone-3 (2%) |
| 7 (9576-029) | TQ (5%) + benzophenone-3 (3%) |
| 8 (9576-030) | TQ (5%) + benzophenone-3 (6%) |
| 9 (9567-073) | TQ (10%) |
| 10 (9567-074) | TQ (10%) + benzophenone-3 (3%) |
| 11 (9567-075) | TQ (10%) + benzophenone-3 (6%) |

These eleven formulations were tested in the following in vitro photostability assay in which thin films of the formulations were applied to a substrate and measured for UV absorption properties following solar simulated UV radiation. First, the solar simulator (Solar Light Solar Simulator Model 600S, Philadelphia, Pa., USA) was warmed up for 20 minutes prior to measurement of fluence rate. The baseline transmission of the Vitro Skin™ samples (IMS, Milford, Conn.) were measured without application of the formulation (n=5 per sample). The formulations were then applied to the Vitro Skin™ samples at an application density of 2 mg/cm$^2$ and spread uniformly over the surface of the sample. The samples were then allowed to dry for 20 minutes before measurement of UV-A absorbance using calibrated Labsphere™ Uv-1000S UV transmission analyzer (Labsphere, North Sutton, N.H., USA). The fluence rate of the solar simulator was measured for the full UW spectrum in terms of W/cm$^2$. The samples were then exposed to 50 J/cm$^2$ of full spectrum radiation from the solar simulator, and the absorbance of the samples were re-measured. The absorbance measures were used to calculate the PFA (biological protection factor in the UVA based). The percentage of the original PFA remaining following the 50J/cm$^2$ of radiation exposure are indicated in Table III.

TABLE III

| FORMULATION NO. | Final % PFA Retention 50 J/CM$^2$ |
|---|---|
| 1 | 13.9 |
| 2 | 53.67 |
| 3 | 59.94 |
| 4 | 44.43 |
| 5 | 67.69 |
| 6 | 70.56 |
| 7 | 72.36 |
| 8 | 86.91 |
| 9 | 44.09 |
| 10 | 67.21 |
| 11 | 74.58 |

As indicated in Table III, the UV-A protection of the dibenzoylmethane derivative UV-A absorber avobenzone without the naphthalene derivative or a benzophenone derivative (Formulation No. 1) was poor following exposure to 50 Joules of radiation (only 13.9% of original PFA remained after exposure). As seen in Formulation Nos. 2 and 3, addition of the benzophenone derivative(oxybenzone) improved the stability of the UV-A protection but did not achieve a 60% level of the original PFA value. Adding the Hallbrite TQ (formulae 4 and 9) was found to also improve the stability of the avobenzone containing sunscreen, but again only reached a 44% level of original PFA protection. Only when the combination of Hallbrite TQ with the benzophenone derivative is used, i.e., formulae Nos. 5, 6, 7, 8, and 10 and 11, and TQ, alone or in combination was the stability enhanced to the level of maintaining at least 60% of the original PFA of the dibenzoylmethane containing sunscreen composition.

As demonstrated by Table III, under rigorous UV exposure conditions of thin films of sunscreen preparations (50 Joules of solar simulated sunlight equivalent to 25 Minimal Erythema Doses) that the combination of all three ingredients provides compositions enhanced photostability.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of stabilizing a composition comprising a dibenzoylmethane derivative UV-A absorbing agent, said method comprising the steps of:

(a) adding to said composition:
  (i) a diester or polyester of a naphthalene dicarboxylic acid; and
  (ii) benzophenone derivative;

(b) exposing said composition to at least 50 Joules/cm$^2$ of sunlight or simulated sunlight;
  wherein (i) and (ii) are present in amounts sufficient to provide a PFA value after said exposing step that is minimally 60% of the PFA value before said exposing step.

2. The method of claim 1, wherein the dibenzoylmethane derivative UV-A absorbing agent is selected from those of the following formula:

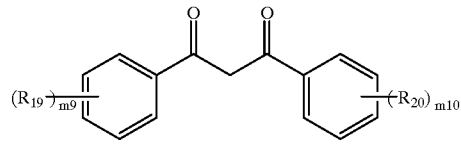

wherein $R_{19}$ and $R_{20}$, independently, are selected from a $C_1$–$C_8$ alkyl, a $C_1$–$C_8$ alkoxy, or mixtures thereof, m9 is a number ranging from 0 to 3, and m10 is a number ranging from 1 to 3.

3. The method of claim 1, wherein said dibenzoylmethane derivative UV-A absorbing agent is selected from the group consisting of: 2-methyldibenzoylmethane, 4-methyldibenzoylmethane, 4-isopropyldibenzoylmethane, 4-tert-butyldibenzoylmethane, 2,4-dimethylbenzoylmethane, 4-tert-butyl-4'-methoxy-dibenzoylmethane, 2,5-dimethylbenzoylmethane, 4,4,'-diisopropylbenzoylmethane, 2-methyl-5-isopropyl-4'-methoxydibenzoylmethane,2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

4. The method of claim 1, wherein said dibenzoylmethane derivative UV-A absorbing agent is 4-tert-butyl-4'-methoxydibenzoylmethane.

5. The method of claim 1, wherein the diester or polyester of a naphthalene dicarboxylic acid is selected from compounds of formulae (X) or (XI) below:

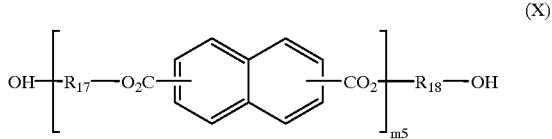

(X)

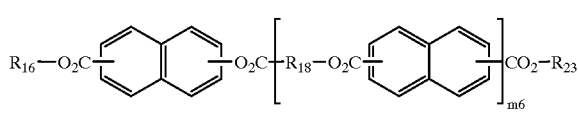

(XI)

wherein $R_{16}$ and $R_{23}$, independently, are selected from the group consisting of a $C_1$-$C_{22}$ alkyl, a diol having the structure HO—$R_{18}$—OH, and a polyglycol having the structure HO—$R_{17}$—(—O—$R_8$-)$_{m5}$—OH; $R_{17}$ and $R_{18}$, independently, are $C_1$-$C_6$ alkenyl; and m5 and m6, independently, are each in the range of 1 to about 100.

6. The method of claim 5, wherein said diester or polyester derivative of a naphthalene dicarboxylic acid is diethylhexyl naphthalate.

7. The method of claim 1, wherein said benzophenone derivative is selected from the group consisting of 2-hydroxy-4-methoxybenzophenone and 2-hydroxy-4-methoxybenzophenone-5-sulfonic acid and 2-2'dihydroxy-4-methoxybenzophenone.

8. The method of claim 1, wherein the dibenzoylmethane derivative UV-A absorbing agent is present in an amount ranging from about 0.1% to about 20%, by weight, of the composition.

9. The method of claim 8, wherein the dibenzoylmethane derivative UV-A absorbing agent is present in an amount ranging from about 0.1 to about 10%, by weight, of the composition.

10. The method of claim 9, wherein the dibenzoylmethane derivative UV-A absorbing agent is present in an amount ranging from about 1 to about 3%, by weight, of the composition.

11. The method of claim 1, wherein the diester or polyester of naphthalene dicarboxylic acid is present in an amount ranging from about 0.1% to about 20%, by weight, of said composition.

12. The method of claim 11, wherein the diester or polyester of naphthalene dicarboxylic acid is present in an amount ranging from about 0.5% to about 10%, by weight, of the composition.

13. The method of claim 1, wherein the benzophenone derivative is present in an amount from about 0.5% to about 6%, by weight, of said composition.

14. The method of claim 13, wherein the benzophenone derivative is present at from about 3 to about 6% by weight.

15. The method of claim 1 further comprising at least one adjunct selected from a UV-B absorbing agent, a cosmetically active agent, antioxidants, chelating agents, preservatives, dyes, opacifiers, pigments, fragrances.

16. The method of claim 15, wherein said UV-B absorbing agent is selected from the group consisting of methyl benzylidene camphor, octyl salicylate, phenylbenzimidazole sulfonic acid, homosalate, titanium dioxide, zinc oxide, dioxybenzophenone, sulisobenzophenone, and dioctyl butamido triazone.

17. The method of claim 15, wherein said cosmetically active agent is present in an amount of from about 0.001% to about 20% by weight of the composition.

18. The method of claim 17, wherein the cosmetically active agent is selected from alkanolamines, hydroxy acids, benzoyl peroxide, sulfur resorcinol, D-panthenol, hydroquinone, anti-inflammatory agents, skin lightening agents, antimicrobial agents, antifungal agents, vitamins, retinoids, hormones, 2-dimethylaminoethanol, lipoic acid, amino acids, lactobionic acid, self-tanning agents, dimethyl aminoethanol, acetyl-coenzyme A, niacin, riboflavin, thiamin, ribose, electron transporters, botanical extracts, and mixtures thereof.

19. The method of claim 18, wherein the hydroxy acids is selected from the group consisting of (i) alpha-hydroxy,(ii) beta-hydroxy acids, (iii) polyhydroxy acids, and (iv) mixtures thereof.

20. A composition comprising:
(a) a dibenzoylmethane derivative UV-A absorbing agent;
(b) a diester or polyester of a naphthalene dicarboxylic acid; and
(c) a benzophenone derivative; wherein the diester or polyester of naphthalene dicarboxylic acid and benzophenone derivative are present in an amount sufficient to provide a PFA value after exposure to at least 50 Joules/cm$^2$ of simulated sunlight that is minimally 60% of the original PFA value before exposure.

21. A method of protecting mammalian skin or hair from UV radiation, comprising the steps of:
(a) providing a composition comprising:
(i) a diester polyester of a naphthalene dicarboxylic acid;
(ii) a benzophenone derivative; and
(iii) a dibenzoylmethane derivative UV-A absorbing agent;
(b) topically applying said composition to said skin or hair; and
(c) exposing said skin or hair to at least 50 Joules/cm$^2$ of simulated sunlight.

* * * * *